United States Patent [19]

Aoyagi et al.

[11] Patent Number: 4,968,539
[45] Date of Patent: Nov. 6, 1990

[54] LIQUID CRYSTAL MEMBRANE

[75] Inventors: Takao Aoyagi, Sagamihara; Shuji Sato, Yachiyo; Minako Yasu, Tokyo; Iwao Nozawa, Funabashi; Yousuke Suzuki, Kawasaki, all of Japan

[73] Assignee: Lion Corporation, Tokyo, Japan

[21] Appl. No.: 277,697

[22] Filed: Nov. 30, 1988

[30] Foreign Application Priority Data

Dec. 1, 1987 [JP] Japan .............................. 62-304123
Dec. 7, 1987 [JP] Japan .............................. 62-309296

[51] Int. Cl.$^5$ ............................................. C09K 19/00
[52] U.S. Cl. ........................................ 428/1; 428/913
[58] Field of Search ...................... 424/448, 449, 443; 428/1, 913

[56] References Cited

U.S. PATENT DOCUMENTS 4,513,034  4/1985  Sparer et al. ........................ 428/1
4,692,336  9/1987  Eckenhoff et al. ................. 424/468

Primary Examiner—Thurman K. Page
Attorney, Agent, or Firm—Burns, Doane, Swecker & Mathis

[57] ABSTRACT

A polymer membrane for delivering a drug is provided. The membrane is capable of regulating the delivery of the drug and comprises (A) a porous hydrophobic polymer membrane having a pore diameter of not larger than 3 μm and a porosity of 10 to 90% which is immobilized with (B) a specific liquid crystal-forming compound having a gel/liquid crystal transition temperature in the range of 25° to 45° C.

6 Claims, 3 Drawing Sheets

LIQUID CRYSTAL MEMBRANE

BACKGROUND OF THE INVENTION

1. Field of the Invention

The present invention relates to a membrane for delivering a drug which membrane is capable of delivering a drug in a suitable manner and, therefore, of delivering the drug in a pattern suitable for the characteristic properties of the drug.

2. Prior Art

Drugs are usually administered in the form of an oral preparation, external preparation, suppository, injection or inhalant depending on the symptoms of the patient, and the pharmacological effect and pharmacokinetical properties of the drug. However, the oral preparations have problems such as irritation of the gastrointestinal system and reduction in the bioavailability due to the so-called first-pass effect in the liver. When a drug is used as an external preparation, problems arise in that the absorption of the drug may be difficult and also that the control of the dose thereof may also be difficult. When a drug is used as a suppository, the absorption of the drug varies depending on the quantity of the fecal matter remaining in the rectum. When a drug is used in an injection, the patient experiences a sharp pain and the continuous use thereof over a long period of time is difficult.

Under these circumstances, intensive studies are being made for the purpose of developing drug delivery systems (DDS). Practically applied the drug delivery systems include external preparations of percutaneous absorption type such as nitroglycerin and nitrous esters for the treatment of angina and scopolamine for the prevention of motion sickness are generally used.

However, these preparations are made only for the purpose of slowly delivering the drug and are essentially different from a DDS capable of controlling the quantity of the drug to be delivered depending on the symptoms.

Recently it was reported that when a membrane comprising a dialkyldimethylammonium bromide deposited on a polymer membrane is used, the diffusion coefficient of a substance in the membrane varies depending on temperature change. These facts are described in, for example, J. American Chem. Soc., 105, No. 15, 4855-4859 (1983) and Chemistry Letters, 645-648 (1979).

However, such a membrane does not respond to only a slight temperature change and the change of the diffusion coefficient in such a case is not so significant. Substances whose diffusion can be controlled by the temperature changes are limited to small ions such as sodium and chlorine ions. Thus, the diffusion of large molecules having pharmacological effects cannot be controlled yet. In addition, a dialkyldimethylammonium bromide deposited on the polymer membrane is ionic and, therefore, it is unsuitable for controlling the delivery of molecules of various ionic drugs.

SUMMARY OF THE INVENTION

Therefore, a primary object of the present invention is to provide a temperature-sensitive polymer membrane for regulating the delivery of a drug capable of sharply responding even to only a slight temperature change, while sufficiently controlling the diffusion of drug molecules and controlling the diffusion of large molecules having a pharmacological effect without exerting any bad influence on ionic drugs. Another object of the present invention is to provide a drug delivery system comprising a combination of a polymer membrane with a heat-generation system for heating, which system is capable of controlling the delivery of a drug according to a physiologically required pattern of the human body for that drug by means of a slight temperature change of the previously controlled heat-generation system for heating.

The inventors have found that a polymer membrane for controlling the delivery of a drug free from the above-described problems can be obtained by immobilizing a liquid crystal-forming compound having special properties on an essentially hydrophobic polymer membrane having a surface free energy or critical surface tension lower than a specified value and that when such a polymer membrane immobilized with the liquid crystal-forming compound is used, the dose of the drug to be applied can be controlled in response even to only a slight temperature change in the application region according to the fever of the inflammatory region or by external heating. The inventors have found further that when the membrane prepared by immobilizing the liquid crystal-forming compound on the polymer membrane is applied to the skin, the barrier effect of the corneous layer is reduced to accelerate the percutaneous absorption of the drug at a given temperature. The present invention has been completed on the basis of these findings.

The present invention provides a membrane for delivering a drug comprising:

(A) a porous hydrophobic polymer membrane having a pore diameter of not larger than 3 μm and a porosity of 10 to 90% which is immobilized with:

(B) a liquid crystal-forming compound having a gel/liquid crystal transition temperature in the range of 25° to 45° C. which is represented by the following general formula (I) or (II):

(I)

(II)

wherein $R_1$, $R_2$ and $R_3$ each represents a hydrogen or an alkyl group having 1 to 6 carbon atoms, $R_4$, $R_5$ and $R_6$ each represents a hydrogen atom, an alkyl group having 6 to 30 carbon atoms or a group of the formula: —$COR_9$, —$COR_{10}$ or —$COR_{11}$ ($R_9$ to $R_{11}$ being each a hydrogen or an alkyl group having 6 to 30 carbon atoms) with the proviso that at least one of $R_4$ to $R_6$ has at least 6 carbon atoms, a, b and c each represents a number of 0 to 20, n represents a number of 0 or 1, $R_7$ represents a hydrogen, an alkyl group having 1 to 30 carbon atoms or a group of the formula: —$COR_{12}$ ($R_{12}$ being a hydrogen or an alkyl group having 1 to 30 carbon atoms), $R_8$ represents a hydrogen, an alkyl group having 1 to 30 carbon atoms or a group of the formula: —$COR_{13}$ ($R_{13}$ being a hydrogen or an alkyl group having 1 to 30 carbon atoms) with the proviso that at least one end portion of the compound of the formula (II) is an alkyl ether or alkyl ester having at least 6 carbon atoms, and d represents a number of 1 to 20.

The present invention also provides a device for regulating the delivery of a drug which comprises a combination of the above-described membrane for delivering drug with (C) a heating member.

DESCRIPTION OF THE PREFERRED EMBODIMENTS

As the liquid crystal-forming molecule-carrying polymer membrane, there is used an essentially porous hydrophobic polymer membrane having a surface free energy or critical surface tension of 45.0 dyn/cm or less. When a hydrophilic polymer membrane is used, the drug molecules leak out through many "water-channels" formed in the polymer matrix, so that delivery of the drug cannot be controlled by the liquid crystal-forming compound in the polymer matrix. The polymer matrix that can be used in the present invention include, for example, polyhexafluoropropylene, polytetrafluoroethylene, polytrifluoroethylene, polyvinylidene fluoride, polyvinyl fluoride, polyethylene, polytrifluorochloroethylene, polystyrene, polyurethane, polypropylene, polyvinyl chloride, polyvinylidene chloride, polyethylene terephthalate, nylon, polydimethylsiloxane, polycarbonates, cellulose acetate, polyethylene vinylacetate, polyethylene vinyl alcohol, polymethyl (meth)acrylate, polyethyl (meth)acrylate, polybutyl (meth)acrylate, polyhexyl (meth)acrylate, polyoctyl (meth)acrylate, polylauryl (meth)acrylate, polystearyl (meth)acrylate, polybutadiene, polybutene, polyisoprene and natural rubber. Among these, those having a surface free energy or critical surface tension of less than 40 dyn/cm are preferred and particularly those having that of less than 35 dyn/cm are preferred. Specifically, polymer compounds having the energy or the tension of 30 dyn/cm are preferable. The polymer membrane preferably has a tensile strength of 10 to 2,000 kg/cm². When the tensile strength thereof is less than 10 kg/cm², it is too soft and when that is more than 2,000 kg/cm², it is too rigid.

A polymer membrane having pores (open cells) of a diameter of 3 μm or less and a porosity of 10 to 90% is used in the present invention. The term "polymer membrane having a pore diameter of 3 μm or less" means a membrane having 30% or less of pores having a diameter of larger than 3 μm. A membrane having pores of an average diameter of 0.001 to 3 μm, particularly 0.01 to 1 μm, is preferred. The porosity of the membrane used can be easily determined with, for example, a mercury porosimeter and it is preferably 20 to 80%. The polymer membrane has a thickness of 1 to 3,000 μm, preferably 10 to 500 μm.

The liquid crystal-forming compounds (B) used in the present invention are those having a gel/liquid crystal transition temperature in the range of 25° to 45° C., particularly compounds of the above general formula (I) or (II) in which at least one of the end hydrogens of the polyalkylene glycol is sealed with a hydrocarbon.

$R_1$ to $R_3$ in the above formula are each preferably a hydrogen or an alkyl group having 2 or 3 carbon atoms. The alkyl groups of $R_4$ to $R_6$ and $R_9$ to $R_{11}$ are preferably those having 12 to 18 carbon atoms. The total of a, b and c is 0 to 60, preferably 1 to 40 and particularly 3 to 20. The alkyl groups of $R_7$, $R_8$, $R_{12}$ and $R_{13}$ are preferably those having 12 to 18 carbon atoms and d is preferably 3 to 12.

Among the liquid crystal-forming compounds of the above formula (I), those wherein at least one of $R_4$, $R_5$ and $R_6$ represents an alkyl group having 6 to 24 carbon atoms include, for example, polyoxyethylene glyceryl monostearyl ether, polyoxyethylene glyceryl distearyl ether, polyoxyethylene glyceryl tristearyl ester, polyoxyethylene glyceryl monomyristyl ether, polyoxyethylene glyceryl dimyristyl ether and polyoxyethylene glyceryl trimyristyl ether.

The liquid crystal-forming compounds of the above formula wherein at least one of $R_4$, $R_5$ and $R_6$ represents —COR (R being an alkyl group having 6 to 24 carbon atoms) include, for example, polyoxyethylene glyceryl monostearate, polyoxyethylene glyceryl distearate, polyoxyethylene glyceryl tristearate, polyoxyethylene trimethylolpropane monostearate, polyoxyethylene trimethylolpropane distearate and polyoxyethylene trimethylolpropane tristearate The compounds of the above formula wherein either $R_7$ or $R_8$ represents a hydrogen include, for example, polyoxyethylene 2-hexyldecyl ether, polyoxyethylene 2-heptylundecyl ether and polyoxyethylene 2-decylpentadecyl ether.

The compounds of the above formula wherein neither $R_7$ nor $R_8$ represents a hydrogen include, for example, polyethylene glycol distearate, polyoxyethylene lauryl ether stearate, polyoxyethylene cetyl ether stearate and polyoxyethylene stearyl ether stearate.

Among them, polyoxyethylene(3 to 5 mol)trimethylolpropane distearate, polyoxyethylene(3 to 10 mol)trimethylolpropane tristearate, polyoxyethylene(4 mol)glyceryl distearate and polyoxyethylene(3 to 20 mol)glyceryl tristearate are preferably used in the present invention.

Among them, the liquid crystal-forming compounds having a gel/liquid crystal transition temperature in the range of 35° to 43° C., particularly 37° to 42° C., are preferred. A gel/liquid crystal transition temperature above body temperature is advantageous, since the diffusion-controlling property of the liquid crystal-forming compound is exhibited at around the gel/liquid crystal transition temperature.

The hydrophobic polymer membrane can be immobilized with the liquid crystal-forming compound by various processes such as (i) adsorption process, (ii) dispersion process and (iii) covalent bond process. In the adsorption process (i), the liquid crystal-forming compound is dissolved in an organic solvent in which this compound is soluble but the polymer is insoluble, then the polymer is immersed in the solution and it is taken out and dried to form the immobilized product. In the dispersion process (ii), the liquid crystal-forming compound is mechanically kneaded in the polymer or alternatively, both liquid crystal-forming compound and polymer are dissolved in an organic solvent in which both of them are soluble and the solution is thoroughly stirred and dried to form the immobilized product. In the covalent bond process (iii), a hydroxyl group of the liquid crystal-forming compound and a functional group (hydroxyl, amino or carboxyl group) in the polymer are bonded together by means of a bifunctional reagent such as a diisocyanate, diglycidyl compound, dicarboxylic acid dichloride or epichlorohydrin to form the immobilized product.

Although the ratio of the liquid crystal-forming compound to the polymer to be immobilized is not particularly limited in the present invention, their weight ratio of is usually 98/2 to 5/95, preferably 90/10 to 10/90 and most particularly 70/30 to 30/70.

The liquid crystal-forming compound is used preferably in an amount larger than the porosity of the polymer membrane, namely an amount sufficient for covering over the pores. The amount is preferably 1 to 3 times as much as the porosity. Thus the drug diffusion coefficient is changed significantly by a slight temperature change and, therefore, the penetration of the drug through the skin is accelerated.

The polymer membrane of the present invention for delivery of a drug comprising components (A) and (B) is usable in various forms. Among them, drug delivery membranes and matrixes for DDS in which the drug delivery rate is controlled depending on changes in body temperature and skin temperature and also on an external thermal stimulation are preferred.

The physiologically active substances (the delivery of which is controlled by the drug delivery polymer membrane of the present invention) include, for example, non-steroidal anti-inflammatory drugs and analgesics such as indomethacin, mefenamic acid, flufenamic acid, diclofenac, ibufenac, alclofenac, metiazinic acid, ibuprofen, ketoprofen, flurbiprofen, benoxaprofen, naproxen, pranoprofen suprofen, fenoprofen, tiaprofen, Y-9213, protizinic acid, Sulindac, phenylbutazone, oxyphenbutazone, ketophenylbutazone, salicylic acid, methyl salicylate, monoglycol salicylate, salicylic acid amide and sodium salicylate; corticosteroids such as hydrocortisone, predonisolone, dexamethasone, fluocinolone acetonide, triamcinolone acetonide, betamethasone valerate, beclometasone dipropionate and betamethasone dipropionate; antibiotics such as tetracycline, chloramphenicol, erythromycin and penicillin; anesthetics such as lidocaine, benzocaine and ethyl aminobenzoate; and antimicrobial such as benzalkonium chloride, nystatin, nitrofurazone, sulfacetamide, clotrimazole, pentamycin, amphotericin B and pyrrolnitrin.

The physiologically active substances include also drugs for treatment of colds such as acetaminophen, ethenzamide, aspirin, diphenhydramine hydrochloride, chlorpheniramine maleate, dextromethorphan hydrobromide, guaiacolsulfonic acid and caffeine. The physiologically active substances include also vasodilators such as nitroglycerin, isosorbide dinitrate, acyl nitrite, nitroerythritol and nitromannitol; and drugs for treatment of hypertension such as clonidine and sympathetic $\beta$-acceptor blocking agents (e.g. propranolol). These physiologically active substances can be used either singly or as a combination of two or more of them, if necessary, depending on their compatibility.

When the membrane of the present invention is used for release rate-limiting membrane of an external preparation, the amount of the medicinal component is controlled to 0.1 to 80% (by weight; the same hereinafter), preferably 0.2 to 50% and the amount of the optional components is 0 to 90%, preferably 0.1 to 80%. It is desirable that the base system excluding the polymer for delivering the drug is as a whole an aqueous system. The base contains at least 1%, preferably at least 5% and particularly at least 10% of water, since when the system contains no water at all, the temperature sensitivity of the drug-delivering polymer membrane of the present invention is poor.

Heating member (C) of the present invention may be any material which can be heated by electricity or the like such as a known heating member comprising a nichrome wire. Among them, a cloth coated with a carbon black-containing paint (trade name: SunFeel®, a product of Marubishi Denko Co., Ltd.) is preferred, since the heating is possible with only small power consumption.

The drug-delivering device of the present invention with the heating member can be used in any desired form such as an external preparation. For example, an impermeable backing layer for inhibiting evaporation of vehicle of drug reservoir is placed on a drug reservoir and further a heat generation system for the heating is provided thereon. The membrane of the present invention for delivering the drug is placed below the drug reservoir layer. A pressure-sensitive adhesive layer for tightly fixing the external preparation on the skin is formed on the whole lower surface of the membrane or the periphery thereof. The drug-delivering polymer membrane of the present invention placed below the drug reservoir layer controls the delivery of the drug in sharp response to the previously set heating pattern of the heat generation system, whereby the quantity of the drug penetration through the skin is controlled.

Figure 1:
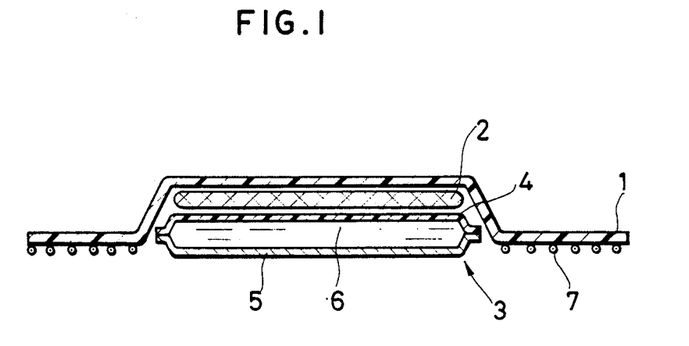
FIGS. 1 and 2 are schematic sectional views of devices of the present invention for regulating the delivery of a drug.

An embodiment of the system is shown in FIG. 1. FIG. 1 is a longitudinal section of the drug-delivering device. A drug reservoir 3 having a heat-generation sheet as the heating member 2 placed thereon is placed inside a backing film 1 which is a sheet of a plastic such as polyvinyl chloride, polyethylene, polypropylene, EVA, EVAL or silicone rubber. The reservoir 3 comprises (1) a film 4 comprising polyvinyl chloride, polyethylene, polypropylene, EVA, EVAL or silicone rubber, (2) a drug-delivering membrane 5 and (3) a drug 6 interposed between (1) and (2). This device is designed so that the drug-delivering membrane 5 is to be applied to the skin of the human body. A pressure-sensitive adhesive 7 is applied to the backing film 1 so that the device can be fixed on the skin. The films 1 and 4 have a thickness of 5 to 500 $\mu$m, preferably 20 to 200 $\mu$m. As the drug 6, a medicinal component which will be described above is kept in the reservoir 3. The drug is in the form of, for example, a gel in which the gel base comprises 40% of ethanol, 21% of propylene glycol, 1% of Carbopol 940, 0.1% of triethanolamine, 0.0002% of EDTA and the balance of water, or in the form of a liquid in which the base comprises 40% of ethanol, 0.0002% of EDTA and the balance of water. Though the thickness of the heating member is not particularly limited, it is usually 10 to 1000 $\mu$m, preferably 20 to 500 $\mu$m. It has a wire connecting to an outside power source. When the heating member 2 is combined with a temperature-controlling member, the delivery of the drug can be controlled more effectively.

In this device wherein the polymer membrane of the present invention for delivering the drug is thus used in combination with the heating member, when the fixed, liquid crystal-forming molecules are heated to a temperature above the gel/liquid crystal transition temperature by the heat-generating sheet, packing of the alkyl chain of the liquid crystal loosens and the diffusion of the drug is changed, thus regulating the delivery of the drug. Namely, the delivery of the drug is regulated by controlling the heating with the heating member and leaving it cool.

The drugs usable in the drug administration system wherein the membrane of the present invention is used are not particularly limited. Particularly when the membrane of the present invention is employed in the production of a plaster for angina, the delivery of the drug can be regulated by controlling the heating, thereby eliminating the side effects and reduction of the medicinal effect heretofore pointed out in the continuous percutaneous administration thereof. From this point of view, nitroglycerol, isosorbide dinitrate, etc. are particularly effective.

When clonidine plaster is used as a hypotenser, three days are required for attaining an effective concentration thereof in the blood. Under these circumstances, there has been need to accelerate the initial percutaneous absorption thereof. When the drug administration system according to the present invention is employed, the percutaneous absorption in the initial stage can be improved by accelerating the delivery by heating.

The optional components usable in the present invention include, for example, polymers such as polydimethylsiloxane, polyethylene glycol, polypropylene glycol, poly(meth)acrylic acid, poly(meth)acrylates, polyvinyl alcohol, polyvinylpyrrolidone, carboxymethylcellulose, alginic acid, alginates and carrageenan; organic solvents such as methyl alcohol, ethyl alcohol, n-propyl alcohol, isopropyl alcohol, n-butyl alcohol, isobutyl alcohol, sec-butyl alcohol, t-butyl alcohol, methyl ethyl ketone, acetone, ethylene glycol, propylene glycol, glycerol, ethyl acetate, 2-pyrrolidone, 1-methyl-2-pyrrolidone, 5-methyl-2-pyrrolidone, 1,5-dimethyl-2-pyrrolidone, 1-ethyl-2-pyrrolidone and 2-pyrrolidone-5-carboxylic acid; percutaneous absorption accelerators such as dimethyl sulfoxide, 1-dodecylazacycloheptane-2-on (trade name: Azone®, dimethyllaurylamide, isosorbitol, dimethylformamide, dodecylpyrrolidone, methionyl sulfoxide, methionyl sulfone, calcium thioglycolate, hydroxyoctyl sulfoxide, cyclohexylmethanol, lysine, arginine, ornithine, histidine, urea, salicylic acid and derivatives thereof, benzyl nicotinate, methoxy polyethylene glycol acrylate, (poly)ethylene glycol glycidyl ether, fatty acid diglycerides having 8 or more carbon atoms, adipic esters, sebacic esters, 1,3-butanediol, 1,4-butanediol and fatty acid ethanolamides; and surfactants such as sodium laurylsulfate, polyoxyethylene lauryl ether, polyoxyethylenesorbitan fatty acid esters and sorbitan fatty acid esters. They can be used either singly or in combinations of two or more.

By using the drug-delivering polymer membrane of the present invention comprising the components (A) and (B), the delivery of the drug in response to the temperature of the affected part is made possible and, in addition, the barrier effect of the corneous layer of the skin is reduced by an interaction between the liquid crystal molecules immobilized in the polymer membrane and the corneous layer to remarkably improve the percutaneous absorption of the drug.

Therefore, by using the drug-delivering membrane as the base material, a self-regulating type external preparation capable of regulating a necessary, sufficient amount of the drug can be provided.

The drug delivering membrane of the present invention can be used in the production of external preparations in various manners. For example, a backing film layer for inhibiting the evaporation of (1) a solution of a physiologically active substance in an organic solvent and (2) water, is placed on a drug reservoir, and the drug-delivering member of the present invention is placed below this drug reservoir. A pressure-sensitive adhesive layer for tightly fixing the external preparation on the skin is formed on the whole lower surface of the membrane or periphery thereof. The drug-delivery polymer membrane of the present invention placed below the drug reservoir regulates the quantity of the physiologically active substance to be delivered in sharp response to temperature change, whereby the quantity of the substance penetrating through the skin is controlled. It is also possible to use micro-capsules comprising a physiologically active substance as the core and the drug-delivering polymer membrane as the membrane material in the production of the external preparation.

When the membrane comprising component (C) in addition to components (A) and (B) is used, the delivery of the drug can be precisely regulated in response even to only a slight temperature change of the system having a previously set heating pattern. Thus, the administration suitable for the physiologically required pattern of the human body for the drug is made possible. For example, temporary washing-out of a drug for angina is made possible and the absorption of a hypotensive drug in the initial stage can be improved.

It is reported in the American Heart Journal, 217–222, July (1984) that it takes three days for a plaster of clonidine (hypotensive drug) to attain an effective concentration thereof in the blood. When the administration system of the present invention is used for the plaster of clonidine, the drug absorption in the initial stage can be improved.

The following examples will further illustrate the present invention, which by no means limit the invention.

EXAMPLES

Example 1

A polypropylene membrane (Celgard® 2402, Hoechst-Celanese Co.; having a pore diameter of 0.02 μm, porosity of 38% and critical surface tension of 35 dyn/cm) was immersed in 20% solution of polyoxyethylene(3 mol) trimethylolpropane tristearate (TPS-303 having a gel/liquid crystal transition temperature of 39.2° C.; a product of Nippon Emulsion Co.), polyoxyethylene(3 mol) glyceryl tristearate (GWS-303 having a gel/liquid crystal transition temperature of 49.2° C.; a product of Nippon Emulsion Co.) or polyoxyethylene-hardened castor oil ether (DC-1-18 having a gel/liquid crystal transition temperature of 0° C. or below; a product of Nikko Chemicals Co.) in chloroform for 1 hour and then air-dried to form a membrane sample.

The membrane samples were mounted in a glass two-chamber diffusion cell. 40% aqueous ethanol solution in which indomethacin had been dissolved (indomethacin concentration: 50 mg/100 ml) was placed in a donor-side chamber and 40% aqueous ethanol solution was placed in a receiver-side chamber. An increase of the indomethacin concentration in the receiver-side chamber with time was determined by HPLC. The diffusion coefficients at 32° C. and 38° C. were determined. The results are summarized in Table 1. The diffusion coefficients are given in terms of $cm^2/sec$ (the same shall apply hereinafter).

TABLE 1

| Liquid crystal-forming compound | Present Invention Polyoxyethylene (3 mol) trimethylpropane tristearate | Comparative Example Glyceryl tristearate | Polyoxyethylene-hardened castor oil ether |
|---|---|---|---|
| Gel/liquid crystal transition temperature | 39.2° C. | 49.2° C. | <0° C. |
| Diffusion coefficient 32° C. | $1.3 \times 10^{-9}$ | $1.9 \times 10^{-8}$ | $4.5 \times 10^{-6}$ |
| 38° C. | $1.6 \times 10^{-7}$ | $2.0 \times 10^{-8}$ | $4.6 \times 10^{-6}$ |
| Ratio | 120 | 1.1 | 1.0 |

It is apparent from Table 1 that when the liquid crystal-forming compounds having a gel/liquid crystal transition temperature not within the range of 25° to 45° C. were used, the ratio of the diffusion coefficient at 38° C. to that at 32° C. was low to indicate that the temperature sensitivity at around the body temperature was insufficient.

Example 2

Teflon membranes having different pore diameters, i.e. Millipore Filter GS (having a pore diameter of 0.22 μm, porosity of 70% and critical surface surface tension of 18.5 dyn/cm), Millipore Filter VS (having a pore diameter of 0.025 μm, porosity of 80% and critical surface tension of 18.5 dyn/cm) and Millipore Filter SM (having a pore diameter of 5 μm, porosity of 80% and critical surface tension of 18.5 dyn/cm) were immersed in 20% solution of polyoxyethylene(a+b+c=5 mol) trimethylolpropane distearate (TPS-205 having a gel/liquid crystal transition temperature of 37° C.; a product of Nippon Emulsion Co.) in chloroform for 1 h and then air-dried to form membrane samples. The adsorption immobilizing rates of the liquid crystal-forming compounds were 73%, 82% and 64%, respectively.

These membranes were mounted in the same diffusion cell as that of Example 1 and the diffusion coefficients were determined in the same manner as that of Example 1. The results are shown in Table 2.

TABLE 2

| | Pore size | Diffusion coefficient 32° C. | 38° C. | Ratio |
|---|---|---|---|---|
| Present Invention | 0.22 μm | $2.9 \times 10^{-8}$ | $2.1 \times 10^{-7}$ | 7.4 |
| | 0.025 μm | $3.2 \times 10^{-8}$ | $8.0 \times 10^{-7}$ | 25.0 |
| Comparative Example | 5.0 μm | $9.8 \times 10^{-8}$ | $1.1 \times 10^{-7}$ | 1.1 |

It is apparent from Table 2 that in the adsorption immobilizing of the liquid crystal-forming compound on the porous hydrophobic polymer membrane, the ratio of the diffusion coefficient at 38° C. to that at 32° C. increased and the temperature-sensitivity of the membrane increased as the pore size of the polymer membrane decreased.

Example 3

Polypropylene membranes (Celgard ® 2402 having a pore diameter of 0.02 μm, porosity of 38% and critical surface tension of 35 dyn/cm) were immersed in 5, 10, 13, 15, 17 and 20% solutions of polyoxyethylene(3 mol)-trimethylolpropane tristearate (TPS-303 of Nippon Emulsion Co. having a gel/liquid crystal transition temperature of 39.2° C.) in chloroform for 1 h and then air-dried to form temperature-sensitive polymer membranes for regulating the delivery of a drug.

These membranes were mounted in the same diffusion cell as that of Example 1 and their diffusion coefficients were determined in the same manner as that of Example 1. The results are shown in Table 3.

TABLE 3

| | Present invention | | | |
|---|---|---|---|---|
| Concentration of solution of TPS-303 in chloroform | 13 | 15 | 17 | 20 |
| Wt. % of TPS-303 in membrane | 31.8% | 35.8% | 38.4% | 48.6% |
| Diffusion coefficient | | | | |
| 32° C. | $2.6 \times 10^{-8}$ | $1.6 \times 10^{-8}$ | $6.7 \times 10^{-9}$ | $1.3 \times 10^{-9}$ |
| 38° C. | $2.2 \times 10^{-7}$ | $1.6 \times 10^{-7}$ | $1.5 \times 10^{-7}$ | $1.6 \times 10^{-7}$ |
| Ratio | 8.5 | 10.5 | 21.8 | 120 |

It is apparent from Table 3 that the ratio of the diffusion coefficient at 38° C. to that at 32° C. increased as the amount (wt.%) of the liquid crystal molecules in the temperature-sensitive membrane increased and particularly that the temperature-sensitivity of the membrane increased when the liquid crystal molecules were immobilized in an amount larger than the porosity of the membrane (namely 38% or more).

Example 4

Polyoxyethylene(3 mol) trimethylolpropane tristearate (TPS-303 of Nippon Emulsion Co. having a gel/liquid crystal transition temperature of 39.2° C.) was fused between two sheets of polypropylene membrane (Celgard ® 2400 of Hoechst-Celanese Co. having a pore diameter of 0.02 μm, porosity of 38% and critical surface tension of 35 dyn/cm). The liquid crystal-forming compound thus directly permeated into the polypropylene membranes and was immobilized on the latter. The whole membrane was pressed (25 t./cm², 10 min.) to form a temperature-sensitive polymer membrane for regulating the delivery of a drug.

Then the temperature-sensitive membrane was mounted in the same diffusion cell as that of Example 1 and the diffusion coefficient thereof was determined in the same manner as that of Example 1.

The results are shown in Table 4.

TABLE 4

| Amount (wt. %) of TPS-303 in membrane | Diffusion coefficient 32° C. | 38° C. | Ratio |
|---|---|---|---|
| 38.1% | $7.1 \times 10^{-1}$ | $1.3 \times 10^{-7}$ | 190 |

It is apparent from Table 4 that the membrane formed by the melt-immobilizing method wherein the molten liquid crystal-forming compound directly permeated into the porous hydrophobic polymer membrane and was immobilized exhibited a high ratio of diffusion coefficient at 38° C. to that at 32° C., and high temperature sensitivity.

Example 5

The skin of the abdomen of WBN/Kob hairless rats ("Saitama" experimental animal) was taken under anesthesia (60 mg/kg pentobarbital, I.P.). A membrane sample prepared in the same manner as that of Example 3 was applied to the corneous layer-side of the skin specimens and they were placed in a glass two-chamber diffusion cell. 10% aqueous ethanol solution containing 2.4% of acetaminophen dissolved therein was placed in a donor-side chamber thereof and a phosphate buffer solution (pH 7.4) was placed in a receiver-side chamber. Increase in acetaminophen concentration in the receiver-side chamber with time was determined by HPLC.

The results are shown in Table 5. It is apparent from Table 5 that when the temperature-sensitive drug-delivering polymer membrane of the present invention was used in this in vitro experiment with skin taken from hairless rats, the permeation rate of acetaminophen through the skin could be controlled in sharp response to the temperature. With this system, TTS for a cold capable of self-regulating the dose of a drug depending on the degree of fever can be developed.

TABLE 5

| Temperature | Test item Amount of drug permeated through the skin ($\mu g/cm^2$) | | | | |
|---|---|---|---|---|---|
| | 2 hr | 4 hr | 12 hr | 24 hr | 36 hr |
| 32° C. | 0 | 0 | 0 | 2 | 5 |
| 38° C. | 1 | 3 | 60 | 170 | 330 |

Example 6

Hair was removed from the abdomen of a white rabbits weighing 2.0 to 2.5 kg with an electric clipper and the abdomen was then shaved with an electric razor carefully so as not to hurt the skin. A glass cell kept at a constant temperature by circulation of warm water was fixed thereon with a quick adhesive (Alon Alpha ® of Toa Gosei Co.) through a membrane sample.

A drug solution was placed in the glass cell and the concentration of the drug in the blood was determined at time intervals over 48 h. In this experiment, the blood sample was taken from the ear vein of the rabbit at given time intervals and the drug concentration was analyzed according to liquid chromatography.

The polymer membrane and the drug solution used in this experiment were prepared as follows: in the example of the present invention, a polypropylene membrane (Celgard ® 2402 having a port diameter of 0.02 $\mu m$ and porosity of 38%) was immersed in 15% or 20% solution of polyoxyethylene(3 mol) trimethylolpropane tristearate (TPS-303 ® of Nippon Emulsion Co.) in chloroform for one hour and then air-dried to obtain the membrane. The drug solution used in this example was 50% aqueous N-methyl-2-pyrrolidone solution further containing 0.01 g/ml of indomethacin.

In a comparative example, about 1 wt.% of indomethacin was mixed in 100 parts by weight of an ointment base comprising 40% of ethyl alcohol, 58.4% of water, 1.5% of a polycarboxylic acid (Carbopol 940 ® of Goodrich Chemical Co.) and 0.1% of triethanolamine to prepare an ointment. 3 g of the ointment was placed in the constant temperature glass cell. No polymer membrane was used.

The results are summarized in Table 6.

TABLE 6

| | | | Concentration of drug in blood (ng/ml) | | |
|---|---|---|---|---|---|
| | | | 6 hr | 24 hr | 48 hr |
| Present invention | Polymer membrane | 38° C. | 20 | 48 | 90 |
| | Liquid crystal | 32° C. | 0 | 11 | 11 |

TABLE 6-continued

| | | | Concentration of drug in blood (ng/ml) | | |
|---|---|---|---|---|---|
| | | | 6 hr | 24 hr | 48 hr |
| | fixing rate 48.1% Polymer membrane | 38° C. | 22 | 55 | 93 |
| | Liquid crystal fixing rate 38.4% | 32° C. | 0 | 15 | 16 |
| Comparative Example | Ointment base | 38° C. | 0 | 2 | 0 |
| | | 32° C. | 0 | 7 | 0 |

It is apparent from the results shown in Table 6 that the polymer membrane of the present invention not only has a high temperature-sensitivity but also provides a high bioavailability.

Example 7

A change of the concentration of ketoprofen in the blood was investigated with the same polymer membrane in the same manner as those of Example 6 except that 3 ml of 30% aqueous ethanol solution in which 0.01 g/ml of ketoprofen had been suspended was used. The results are shown in Table 7.

TABLE 7

| | | Concentration of drug in blood (ng/ml) | | |
|---|---|---|---|---|
| | | 6 hr | 24 hr | 48 hr |
| Temperature | 38° C. | 740 | 410 | 300 |
| | 32° C. | 0 | 18 | 17 |

Thus according to the present invention, high temperature sensitivity and high bioavailability can be attained.

Example 8

The same membrane sample as that of Example 2 and the same skin of hairless rat as that of Example 3 were mounted in the glass 2-chamber diffusion cell in the same manner as described above. 0.1% aqueous nitroglycerin solution was placed in the donor-side chamber and a phosphate buffer solution (pH 7.4) was placed in the receiver chamber. An increase of the concentration of nitroglycerin in the receiver chamber with time was determined by HPLC. As a control, only the skin free from the sample membrane was used in the experiment of the permeation of nitroglycerin through the skin. The experiment was conducted at 38° C.

The changes with time are shown in Table 8. It is apparent from Table 8 that when the membrane sample was used in combination with the skin taken from the hairless rat, the drug permeated more easily through the skin than through only the skin. The effect of the membrane sample for accelerating the percutaneous absorption of the drug was thus proved.

TABLE 8

| Membrane | Test Cumulative amount of permeated nitroglycerin ($\mu g/cm^2$) | | | | |
|---|---|---|---|---|---|
| | 2 h | 4 hr | 6 hr | 8 hr | 10 hr |
| With polymer membrane of the present invention | 26 | 92 | 185 | 274 | 365 |
| Without polymer membrane of the present invention | 8 | 44 | 101 | 154 | 218 |

Example 9

Molten polyoxyethylene (3 mol) trimethylolpropane tristearate (TPS-303 of Nippon Emulsion Co. having a gel/liquid crystal transition temperature of 39.2° C.) was interposed between two sheets of polypropylene membrane (Celgard ® 2400 having a pore diameter of 0.02 μm, porosity of 38% and critical surface tension of 35 dyn/cm). The liquid crystal-forming compound thus penetrated directly into the polypropylene membrane, whereby the former was immobilized on the latter. The whole membrane was pressed (25 t/cm$^2$, 10 min.) to form a temperature-sensitive drug delivery-regulating polymer membrane. The immobilizing rate of TPS-303 on the polymer membrane thus obtained was 38.1 wt.%.

Figure 2:
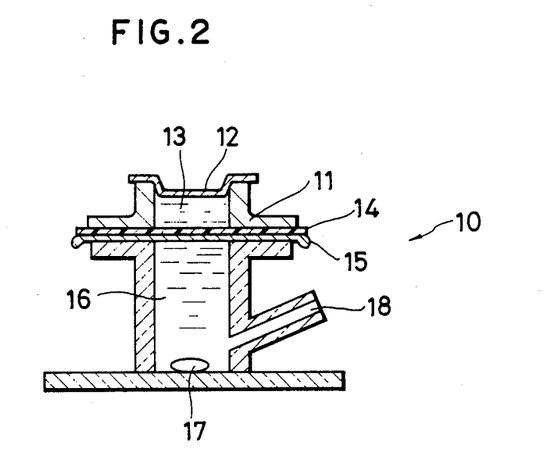

The temperature-sensitive drug delivery-regulating polymer membrane was then mounted in a glass vertical-type diffusion cell 10. 5 ml of 2.5% isosorbide dinitrate solution 13 (the base solution comprised water and ethyl alcohol in a weight ratio of 60/40) was placed thereon. 13 ml of the above-mentioned base solution 16 was placed in the lower receiver-chamber. A heat-generation sheet 12 was placed over the drug solution.

FIG. 2 is a schematic sectional view of the device used herein. In this device, a heating sheet 12 was placed above a cylindrical member 11. The isosorbide dinitrate solution 13 was placed below the heating sheet 12 and a drug delivery-regulating polymer membrane 14 was placed below the solution 13. A stirrer 17 was arranged on the receiver side to stir the base solution. The base solution was taken out through an outlet 18 at time intervals to determine the quantity of isosorbide dinitrate. Although another membrane 15 is shown in FIG. 2, this membrane was omitted in the experiment in Example 9.

Figure 3:
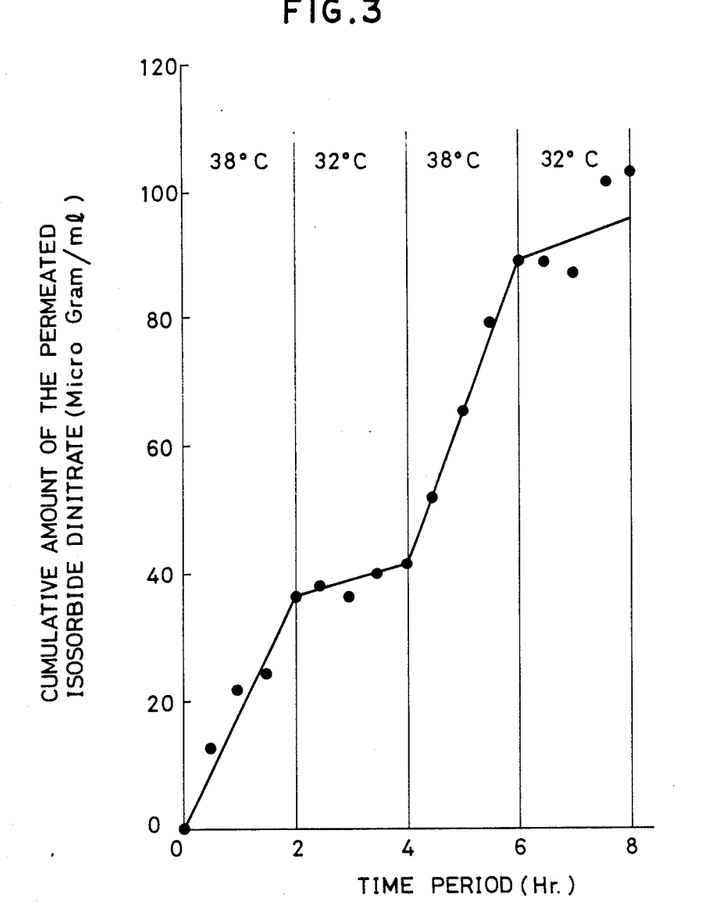
FIGS. 3 and 4 show the control of the delivery of a drug with the devices of the present invention.

The heat generation sheet 12 (SunFeel ® of Marubishi Denko Co.) had a heating element size of 6 cm$^2$, the heating element resistance of 105 Ω and rated voltage of 3.0 V. Two dry cells of 1.5 V were used as the electric source. The heating and cooling (namely, discombination of heating) were repeated intermittently at intervals of 2 h. The cumulative amount of the permeated drug on the receiver-side of the diffusion cell is shown in FIG. 3. It is apparent from FIG. 3 that the drug delivery pattern can be regulated suitably by controlling the temperature of the heat generation system.

Example 10

The skin of the abdomen of WBN/Kob hairless rats ("Saitama" experimental animal) was taken under anesthesia (60 mg/kg pentobarbital sodium, I.P.). The membrane sample of Example 9 was applied to the corneous layer-side of the skin specimens and they were mounted in a glass vertical-type diffusion cell shown in FIG. 2 (the skin was indicated as 15). 5 ml of 2.5% isosorbide dinitrate solution (the base solution comprised water and ethyl alcohol in a weight ratio of 60/40) was placed in the cell placed thereon. The solution was covered with the same heat-generation sheet as that of Example 9. The heating to 38° C and cooling were repeated intermittently at intervals of 6 h. The cumulative amount of the permeated drug on the receiver-side of the diffusion cell is shown in FIG. 4.

Figure 4:
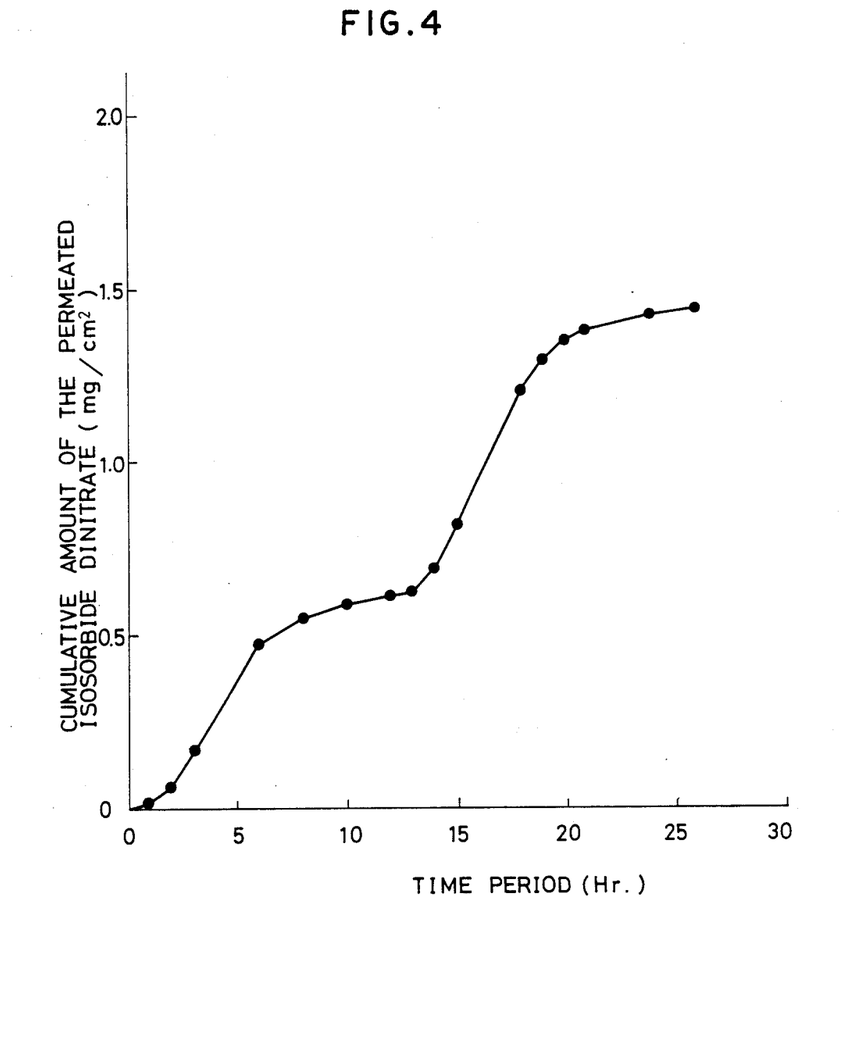

It is apparent from FIG. 4 that the permeation pattern of the drug through the skin can be regulated suitably by controlling the temperature of the heat generation system.

Example 11

A drug reservoir (4 cm$^2$) was prepared by heat-sealing the same drug delivery-regulating membrane as that of Example 9 with a polyethylene membrane as the impermeable backing film. 3 g of an ointment comprising about 2.4% of isosorbide dinitrate in 100 parts by weight of an ointment base comprising 40% of ethyl alcohol, 58.4% of water, 1.5% of polycarboxylic acid (Carbopol 940 ® of Goodrich Chemical Co.) and 0.1% of triethanolamine was placed in drug reservoir.

Hair was removed from the abdomen of white rabbits weighing 2.0 to 2.5 kg with an electric clipper and the abdomen was then shaved with an electric razor carefully so as not to hurt the skin. The drug reservoir was placed thereon in such a manner that the drug delivery-regulating membrane was brought in contact with the skin. The drug reservoir was then covered with the same heat generation sheet as that of Example 9 and the sheet was fixed with an adhesive tape as shown in FIG. 1.

The heating was conducted from 0 to 10 h after the initiation and then from 20 to 30 h after that. The temperature was kept at 38° C. or above during the heating. The blood sample was taken from the ear vein of the rabbit at given time intervals and the drug concentration in the blood was analyzed according to liquid chromatography. The results are shown in Table 9. It is apparent from Table 9 that the concentration of isosorbide dinitrate in the blood was high after heating for 10 h (10 h and 30 h after the initiation of the heating) and low after leaving to cool (20 h and 40 h after the initiation of the heating). This fact indicated that the concentration of the drug in the blood can be controlled in response to the system.

TABLE 9

| Time (hr) | 10 | 20 | 30 | 40 |
|---|---|---|---|---|
| Concentration in blood (ng/ml) | 280 | 135 | 302 | 158 |

What is claimed is:

1. A membrane for delivering a drug comprising:
(A) a porous hydrophobic polymer membrane having a pore diameter of not larger than 3 μm and a porosity of 10 to 90% which is immobilized with;
(B) a liquid crystal-forming compound having a gel/liquid crystal transition temperature in the range of 25 to 45° C. which is represented by the following general formula (I):

wherein $R_1$, $R_2$ and $R_3$ each represent a hydrogen or an alkyl group having 1 to 6 carbon atoms, $R_4$, $R_5$ and $R_6$ each represent a hydrogen atom, an alkyl group having 6 to 30 carbon atoms or a group of the formula: $-COR_9$, $-COR_{10}$ or $-COR_{11}$ wherein $R_9$ to $R_{11}$ are each a hydrogen or an alkyl group having 6 to 30 carbon atoms with the proviso that at least one or $R_4$ to $R_6$ has at least 6 carbon atoms, a, b, and c each represent a number from 0 to 20, n represents a number of 0 or 1, wherein the weight ratio of the liquid crystal forming compound (B) to the hydrophobic polymer membrane (A) is 98/2 to 5/95 and the amount of crystal-forming compound (B) is 1 to 3 times the amount of the porosity of the polymer membrane (A).

2. The membrane for delivering a drug according to claim 1, wherein the polymer membrane is made of a substance selected from the group consisting of polyhexafluoropropylene, polytetrafluoroethylene, polytrifluoroethylene, polyvinylidene fluoride, polyvinyl fluoride, polyethylene, polytrifluorochloroethylene, polystyrene, polyurethane, polypropylene, polyvinyl chloride, polyvinylidene chloride, polyethylene terephthalate, nylon, polydimethylsiloxane, polycarbonates cellulose acetate, polyethylene vinylacetate, polyethylene vinyl alcohol, polymethyl (meth)acrylate, polyethyl (meth)acrylate, polybutyl (meth)acrylate, polyhexyl (meth)acrylate, polyoctyl (meth)acrylate, polylauryl (meth)acrylate, polystearyl (meth)acrylate, polybutadiene, polybutene, polyisoprene and natural rubber.

3. The membrane for delivering a drug according to claim 1, wherein the liquid crystal-forming compound is that of the formula (I) wherein $R_1$ to $R_3$ each represent a hydrogen or an alkyl group having 2 or 3 carbon atoms, $R_4$ to $R_6$ and $R_9$ to $R_{11}$ each represent an alkyl group having 12 to 18 carbon atoms and the total of a, b and c is 0 to 60.

4. The membrane for delivering a drug according to claim 1, wherein the liquid crystal-forming compound is immobilized to the membrane by absorbing it from a solution containing the liquid crystal-forming compound.

5. The membrane for delivering a drug according to claim 1, wherein the liquid crystal-forming compound is immobilized to the membrane by sandwiching it between the membranes.

6. The membrane for delivering a drug according to claim 1, which is combined with a heating member.

* * * * *